United States Patent [19]

Holdt et al.

[11] Patent Number: 4,578,207

[45] Date of Patent: Mar. 25, 1986

[54] TWO COMPONENT CLEANER AND DISINFECTANT TABLET

[75] Inventors: Bernd-Dieter Holdt, Düsseldorf; Ronald Menke, Mettmann; Gerd Praus, Krefeld; Petra Hasselbach, Düsseldorf, all of Fed. Rep. of Germany

[73] Assignee: Henkel Kommanditgesellschaft auf Aktien, Düsseldorf, Fed. Rep. of Germany

[21] Appl. No.: 561,285

[22] Filed: Dec. 14, 1983

Related U.S. Application Data

[63] Continuation-in-part of Ser. No. 452,943, Dec. 27, 1982, abandoned.

[30] Foreign Application Priority Data

Jul. 7, 1982 [DE] Fed. Rep. of Germany ....... 3225292

[51] Int. Cl.[4] ............................................. C11D 17/00
[52] U.S. Cl. ...................................... 252/134; 252/96; 252/98; 252/106; 252/174; 252/546; 252/558; 252/559; 252/174.23; 4/227; 4/228
[58] Field of Search ................... 252/134, 174, 174.23, 252/DIG. 16, 96; 4/227, 228

[56] References Cited

U.S. PATENT DOCUMENTS

| | | | |
|---|---|---|---|
| 2,174,779 | 10/1939 | Delorme | 18/13 |
| 3,294,692 | 12/1966 | Kelly et al. | 252/134 |
| 3,925,225 | 12/1975 | Morrison | 252/134 |
| 4,200,606 | 4/1980 | Kitko | 4/227 |
| 4,256,599 | 3/1981 | Krisp et al. | 252/174 |
| 4,269,723 | 5/1981 | Barford et al. | 252/174 |
| 4,318,878 | 3/1982 | Hoernig | 264/148 |

FOREIGN PATENT DOCUMENTS

| | | |
|---|---|---|
| 0013043 | 12/1979 | European Pat. Off. |
| 0055100 | 6/1982 | European Pat. Off. |
| 977194 | 4/1951 | France |

*Primary Examiner*—Paul Lieberman
*Assistant Examiner*—Hoa Van Le
*Attorney, Agent, or Firm*—Ernest G. Szoke; Nelson Littell, Jr.

[57] ABSTRACT

A two component tablet for cleaning and disinfecting toilet flush tanks which adhere to the tank and will not be washed away and/or decomposed comprising extruded component A consisting essentially of (a) 25 to 50% by weight of an alkylbenzene sulfonate, (b) 0 to 40% by weight of inorganic alkali metal salts, (c) 0 to 10% by weight of at least one plasticizer, (d) 5 to 20% by weight of at least one disintegration rate regulator selected from the group consisting of fatty acid ethanolamides, fatty acid diethanolamides and stearic acid, (e) 0 to 50% of a chlorine releasing compound or acid and (f) 0 to 30% by weight of a complexing agent with the sum of (e) and (f) being greater than 5% and component B consisting essentially of (a') 30 to 55% by weight of an alkylbenzene sulfonate (b') 15 to 45% by weight of inorganic alkali metal salts, (c') 0 to 10% by weight of at least one plasticizer, (d') 10 to 15% by weight of at least one disintegration rate regulator selected from the group consisting of fatty acid ethanolamides, fatty acid diethanolamides and stearic acid, (e') 1 to 10% by weight of perfume and (f') 5 to 15% by weight of dye, the sum of (c') and (e') being not greater than 10%, components A and B occupying different portions of the final tablet.

1 Claim, 1 Drawing Figure

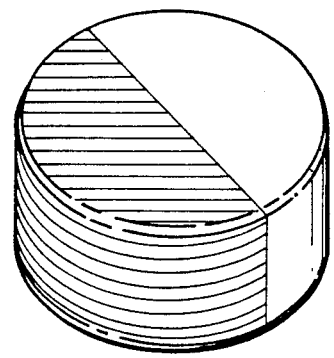

TWO COMPONENT CLEANER AND DISINFECTANT TABLET

PRIOR APPLICATION

This application is a continuation-in-part of our co-pending, commonly assigned U.S. patent application Ser. No. 452,943 filed Dec. 27, 1982, now abandoned.

STATE OF THE ART

Cleaner and disinfectant pieces in the form of tablets for use in the water tank of flush toilets are known. Such tablets consist generally of compositions containing components selected from the group consisting of tensides, disinfectants, bleaches, salts, acids, complexing agents, builders, dyes, fragrances, disintegration rate regulators, plasticizers, and, optionally, other substances. The production of such tablets starts preferably with compositions that are plasticizable and can be extruded in the form of a strip. The tablets are obtained by cutting the strip.

It is understood that a combination of active substances that can react with each other during an extended storage or are otherwise incompatible, is not obtainable in conventional tablets. As a solution, multi-chamber dispensers which can hold tablets of different compositions of active ingredients that are not compatible with each other have been suggested for hanging in the water tank.

The respective solutions of active substances are prepared and stored separately in such dispensers and are combined with each other only during the flushing action. An example of this is described in EP No. A 13 043, which concerns the combined application of disinfecting hypochlorites and hypochlorite sensitive dyes. However, the production of such dispenser is technically demanding and expensive. The handling of separate agents is inconvenient for the user.

EPO application No. 0,055,100 describes two component blocks for toilet tanks wherein small individual tablets are inserted into the main body of the block but the assembly thereof is complicated and the blocks tend to decompose into their dissimilar parts before or after contact with water and are then easily flushed away.

OBJECTS OF THE INVENTION

It is an object of the invention to provide cleaner and disinfectant tablets suitable for use in toilet flush tanks.

It is another object of the invention to provide a cleaner and disinfectant tablet which has an improved shelf life.

It is a further object of the invention to provide a two component cleaner and disinfectant tablet in which each component contains one or more substances which are antagonistic to those of the other but which are in a form which minimizes their premature interaction.

It is an additional object of the invention to provide or improved, prolonged method of disinfecting and cleaning toilet flush tanks and urinals.

These and other objects and advantages of the invention will become more obvious from the following detailed description.

THE INVENTION

The novel two-component cleaning and disinfecting tablets for urinals and toilet flush tanks are comprised of extruded component A consisting essentially of (a) 25 to 50% by weight of an alkylbenzene sulfonate, (b) 0 to 40% by weight of inorganic alkali metal salts, (c) 0 to 10% by weight of at least one plasticizer, (d) 5 to 20% by weight of at least one disintegration rate regulator selected from the group consisting of fatty acid ethanolamides, fatty acid diethanolamies and stearic acid, (e) 0 to 50% of a chlorine releasing compound or acid and (f) 0 to 30% by weight of a complexing agent with the sum of (e) and (f) being greater than 5% and component B consisting essentially of (a') 30 to 55% by weight of an alkylbenzene sulfonate, (b') 15 to 45% by weight of inorganic alkali metal salts, (c') 0 to 10% by weight of at least one plasticizer, (d') 10 to 15% by weight of at least one disintegration rate regulator selected from the group consisting of fatty acid ethanolamides, fatty acid diethanolamides and stearic acid, (e') 1 to 10% by weight of perfume and (f') 5 to 15% by weight of dye, the sum of (c') and (e') being not greater than 10%, components A and B occupying different portions of the final tablet.

The tablets of the invention are two component cakes which will not decompose into smaller parts since the components contain similar ingredients and they adhere well to one another. The use of alkylbenzene sulfonates and the particular disintegration rate regulators is critical to obtain these results. The tablets in use adhere to the side wall or bottomm of the urinal or flush tank and can not be flushed away. Moreover, the tablets are produced by a simple, economical process.

The novel process of the invention for the preparation of the two-component cleaning and disintegrating tablets comprises separately admixing the ingredients of components A and B separately extruding the components into strips or rods, combining the strips or rods of components A and B into a single element and cutting the said element into pieces, preferably pieces weighing 20 to 200, preferably about 50, grams. The drawing shows such a two component tablet. The extrudable mixtures preferably have the same or a similar viscosity and the extrusion and combining of the strips is performed advantageouly in one operation, e.g. with the aid of the double extrusion press with suitable dies.

The word "tablets" is understood to mean formed pieces of any dimension that can be obtained by cutting the extruded strip into cross sections and especially the ratio of diameter to thickness may be varied as desired. The tablet's ratio of area to thickness should be not less than 1, preferably 1 to 5: 1, for the stable positioning of the tablet on the bottom of the toilet flush tank. The tablet is essentially planar as shown in the drawing.

The invention is used especially for those combinations of active substances that contain, in addition to a dye, a disinfectant based on substances releasing active chlorine. Almost all suitable dyes, mainly green and blue shades, with the exception of a few triphenylmethane dyes, are sensitive to chlorine and change their color more or less rapidly in the presence of hypochlorite, or fade out. However, an addition of dye to cleaner and disinfectant tablets for the water tank is desirable, not only because the colored rinse solution provides an impression of cleanliness and hygiene, but since the absence of color usually indicates that the tablet is no longer effective.

Another area of application for the invention is with combinations of active substances that contain sensitive dyes and fragrances in addition to a large proportion of acids or complexing agents to prevent lime, rust or urine deposits. Especially the choice of fragrances for the perfuming of toilet cleaners is normally very limited by the great sensitivity of most fragrances to acids. Complexing agents in high concentrations can also damage certain dyes and fragrances.

A particular advantage of the invention is also seen in the possibility that the dyes or a component containing dyes or other reactive substances can be located in the center of the tablet by the use of coaxial screw presses for the extrusion, for example, which makes handling simpler and safer for the consumer and makes the need for a special tablet coating superfluous.

The novel method of the invention of cleaning and disinfecting urinals and toilet flush tanks comprises adding to the urinal or toilet flush tank a tablet of the invention.

In the following examples there are described several preferred embodiments to illustrate the invention. However, it is to be understood that the invention is not intended to be limited to the specific embodiments.

EXAMPLE 1

CLEANING AND DISINFECTANT TABLET THAT RELEASES ACTIVE CHLORINE

This example concerns a cleaner and disinfectant tablet that is composed of two extrudable compositions, one of which contains a substance that releases active chlorine, the other a dye sensitive to chlorine. The dyes are preferably of the type that are soluble in water and do not adhere to ceramic surfaces, e.g. triphenylmethane dyes or triarylmethane dyes, such as disulfide blue. The coloring is needed as a signal to the user that the tablet is functioning properly. An absence of color indicates that the active substances have been used up. Suitable as chlorine releasing disinfectants are sodium dichloroisocyanurate, [(Monotrichloro)-tetra(-monopotassium dichloro)]-pentaisocyanurate, dichlorodimethyl hydrantoin, etc.

The range of composition for such a preferred tablet consisting of two extrudable compositions (A) and (B) is the following: (All components of the compositions are given in % by weight unless otherwise indicated.)

| (A) Disinfectant containing Component | |
|---|---|
| (a) alkylbenzene sulfonate | 25–40 |
| (b) inorganic alkali metal salts | 20–30 |
| (c) plasticizers | 5–10 |
| (d) disintegration rate regulating agents | 10–20 |
| (e) active chlorine releasing disinfectant | 5–30 |
| (B) Dye containing Component | |
| (a') alkylbenzene sulfonate | 30–40 |
| (b') inorganic alkali metal salts | 30–45 |
| (c') plasticizers | 5–10 |
| (d') disintegration rate regulating agents | 10–15 |
| (e') perfume | 1–10 |
| (f') | 5–15 | wherein the sum of c' and e' does not exceed 10 weight %

The sulfonate contained in the formulations given above is a readily soluble, sudsing alkylbenzene sulfonate (ABS). The combination of alkalimetal salts and ABS aids the adhesion of the tablets to the bottom of the flush tank to a large degree. This factor guarantees safe use even with a fast filling and draining action of the water.

The plasticizers, which affect the visosity, are mainly perfume oils, liquid paraffin, 1,2-propylene glycol, silicone oil, dibutyl phthalate, monoethylene glycol, citrus terpenes and diethyl phthalate. Where all perfumes act as plasticizers, it is well understood, that only those can be used in both components of the tablet, that are insensitive to decomposition by other ingredients. An advantage may be the use of plasticizers that are not miscible with each other, to avoid migration of the dye from the colored phase to the colorless phase.

A special formulation has the following composition:

| Composition (A) with Chlorine source | |
|---|---|
| Sodium dodecylbenzene sulfonate with 20% sodium carbonate | 32.0 |
| Sodium sulfate, anhydrous | 10.0 |
| Sodium tripolyphosphate | 13.0 |
| Sodium dichloroisocyanurate dihydrate | 20.0 |
| Stearic acid | 15.0 |
| Pine oil fragrance | 10.0 |
| Composition (B) with Dye | |
| Sodium dodecylbenzene sulfonate with 20% sodium carbonate | 39.5 |
| Sodium sulfate, anhydrous | 21.0 |
| Sodium tripolyphosphate | 13.0 |
| Monoethanolamide of coco-fatty acids | 7.0 |
| Stearic acid | 3.5 |
| Dye | 10.0 |
| Pine oil fragrance | 6.0 |

This type of tablet is produced preferably with a coaxial extruding press, to place the composition containing the dye in the center of the extruded strip. The strip is cut into sections with an individual weight of about 50 grams, about half of which is composition A and about half is composition B.

EXAMPLE 2

HEAVY DUTY CLEANING TABLET WITH HIGH ACID CONTENT, COMPOSITION (A), DYE AND FRAGRANCE COMPOSITION (B) TO PREVENT DEPOSITS OF LIME, RUST AND URINE

A relatively high acid content is desirable to prevent deposits of lime, rust and/or urine. A color indicator and a fragrance are also necessary. The selection of the latter is usually very limited because of the high sensitivity of most fragrances to acid. The 2 component tablet represents an advantageous solution also to this problem since acid and fragrance are contained in compositions which are kept generally separate from each other.

Compositions of this type containing an acid preferably consist of the following A and B components

| | Weight % |
|---|---|
| Component A | |
| (a) alkylbenzene sulfonate | 30–50 |
| (b) inorganic alkali metal salts | 0–40 |
| (c) plasticizers | 0–10 |
| (d) disintegration rate regulators | 5–15 |
| (e) acid | 10–50 |
| Component B | |
| (a') alkylbenzene sulfonate | 40–55 |
| (b') inorganic alkali metal salts | 15–30 |
| (c') plasticizers | 0–10 |
| (d') disintegration rate regulators | 10–15 |
| (e') perfume | 1–10 |
| (f') dye | 5–15 | wherein the sum of c and e does not exceed 10 weight %.

Preferably the acid in component A is taken out of the group consisting of amidosulfonic acid, sodium bisulfate, citric acid, and phosphoric acid, and mixtures thereof.

The following examples describe specific compositions for 2 component tablets with a composition (A) that contains an acid component and a tenside composition, while composition (B) contains a tenside composition, a fragrance and dye.

| Composition (A) with the Acid Component Amidosulfonic Acid | |
|---|---|
| Sodium dodecylbenzene sulfonate | 30.0 |
| Monoethanolamide of coco-fatty acids | 7.0 |
| Stearic acid | 8.0 |
| Liquid paraffin | 5.0 |
| Amidosulfonic acid | 50.0 |
| or | |
| Composition (A) with the Acid Component Citric Acid | |
| Sodium dodecylbenzene sulfonate | 44.0 |
| Monoethanolamide of coco-fatty acids | 7.0 |
| Stearic acid | 3.0 |
| Diethyl phthalate | 6.0 |
| Citric acid | 40.0 |
| Composition (B) with Acid Sensitive Fragrance | |
| Sodium dodecylbenzene sulfonate | 52.0 |
| Monoethanolamide of coco-fatty acids | 7.0 |
| Stearic acid | 3.0 |
| Sodium sulfate, anhydrous | 10.0 |
| Sodium tripolyphosphate | 10.0 |
| Dye | 8.0 |
| Acid sensitive fragrance | 10.0 |

The dye is insoluble in compositions (A) which prevents a migration of the dye from composition (B) to the acid containing composition (A).

The tablets have a preferred weight of about 50 to 100 grams.

Another tablet based on phosphoric acid, which has a similar effect, has the following composition:

| Composition (A) with Acid Component | |
|---|---|
| Sodium dodecylbenzene sulfonate | 38.0 |
| Sodium sulfate, anhydrous | 37.0 |
| Monoethanolamide of coco-fatty acids | 7.0 |
| Stearic acid | 3.0 |
| Phosphoric acid, 85% | 15.0 |
| Composition (B) with Acid-Sensitive Fragrance | |
| Sodium dodecylbenzene sulfonate | 48.5 |
| Monoethanolamide of coco-fatty acids | 7.0 |
| Stearic acid | 3.5 |
| Sodium sulfate, anhydrous | 15.0 |
| Sodium tripolyphosphate | 10.0 |
| Dye | 8.0 |
| Acid sensitive fragrance | 8.0 |

The tablets can be prepared by simultaneous extrusion of compositions (A) and (B) in a double-screw press, which provides for the combining of the two strips, and the shaping e.g. round or rectangular, through a suitable die. The shaped, combined strips are cut into sections having a weight of from 50 to 100 grams.

EXAMPLE 3

TWO PHASE TABLET WITH IMPROVED PREVENTION OF LIME AND RUST DEPOSITS WITH A BASE OF COMPLEXING AGENT

A high concentration of complexing agents is needed for the prevention of lime and rust deposits in toilet bowls. Although certain formulations of these substances also impair specific dyes and fragrances, the two component tablet permits a combination. For example, composition (A) may contain a complexing agent or dispersing agent for hard-water specific deposits in a high concentration, and compositions (B) a combination of a tenside composition, a fragrance and a dye. Compositions of this type containing complexing agents preferably consist of the following A and B components.

| | Weight % |
|---|---|
| Component A | |
| (a) alkylbenzene sulfonate | 30–50 |
| (b) inorganic alkali metal salts | 20–35 |
| (c) plasticizers | 5–10 |
| (d) disintegration rate regulators | 5–15 |
| (f) complexing agent | 5–30 |
| Component B | |
| (a') alkylbenzene sulfonate | 30–50 |
| (b') inorganic alkali metal salts | 30–45 |
| (c') plasticizers | 0–10 |
| (d') disintegration rate regulators | 10–15 |
| (e') perfume | 1–10 |
| (f') dye | 5–15 | wherein the sum of c and e does not exceed 10%.

Preferably the complexing or lime dispersing agent is of the group EDTA, NTA, polycarboxylic acid and mixtures thereof.

A specific formulation of such a two component tablet is given by the following:

| Composition (A) with EDTA Complexing Agent | |
|---|---|
| Sodium dodecylbenzene sulfonate with 20% sodium carbonate | 46.0 |
| Sodium sulfate, anhydrous | 25.0 |
| Diethanolamide of oleic acid | 6.0 |
| Stearic acid | 6.0 |
| EDTA Sodium salt | 15.0 |
| Honeysuckle fragrance (Chevrefeuille Super 81-2467) | 2.0 |
| Composition (B) with Dye | |
| Sodium dodecylbenzene sulfonate with 20% sodium carbonate | 42.0 |
| Sodium sulfate, anhydrous | 18.0 |
| Sodium tripolyphosphate | 15.0 |
| Diethanolamide of oleic acid | 6.0 |
| Stearic acid | 7.0 |
| Dye | 10.0 |
| Honeysuckle fragrance (Chevrefeuille Super 81-2487) | 2.0 |

The product is prepared by extrusion and cutting into sections, as described in Example 2.

Various modifications of the compositions and methods of the invention may be made without departing from the spirit or scope thereof and it is to be understood that the invention is to be limited only as defined in the appended claims.

What we claim is:

1. A two-component cleaning and disinfecting tablet for urinals and toilet flush tanks comprising extruded component A consisting essentially of (a) 25 to 50% by weight of an alkylbenzene sulfonate, (b) 20 to 30% by weight of inorganic alkali metal salts, (c) 5 to 10% by weight of at least one plasticizer, (d) 10 to 20 by a weight of at least one disintegration rate regulator selected from the group consisting of fatty acid ethanolamides, fatty acid diethanolamides and stearic acid, and (e) 5 to 30% by weight of a chlorine releasing compound and extruded component B consisting essentially of (a') 30 to 40% by weight of an alkylbenzene sulfonate, (b') 30 to 45% by weight of inorganic alkali metal salts, (c') 0 to 10% by weight of at least one plasticizer, (d') 10 to 15% by weight of at least one disintegration rate regulator selected from the group consisting of fatty acid ethanolamides, fatty acid diethanolamides and stearic acid, (e') 1 to 10% by weight of perfume and (f') 5 to 15% by weight of dye, the sum of (c') and (e') being not greater than 10% by weight, components A and B being attached together and occupying different portions of the final tablet.

* * * * *